United States Patent
Perronnet et al.

[11] 4,000,291
[45] Dec. 28, 1976

[54] OXAZOLIDINE, 2-4 DIONES USEFUL AS ANTIANDROGENICS

[75] Inventors: Jacques Perronnet, Paris; Claude Bonne, Bry-sur-Marne, both of France

[73] Assignee: Roussel-UCLAF, Paris, France

[22] Filed: June 10, 1975

[21] Appl. No.: 585,718

[30] Foreign Application Priority Data
June 21, 1974  France .............................. 74.21603

[52] U.S. Cl. .............................................. 424/272
[51] Int. Cl.² ...................... A01N 9/22; A01N 9/28
[58] Field of Search ................................... 424/272

[56] References Cited
UNITED STATES PATENTS

| | | | |
|---|---|---|---|
| 2,909,467 | 9/1959 | Shapiro et al. ..................... | 424/272 |
| 3,655,687 | 4/1972 | Fausan et al. ...................... | 424/272 |
| 3,703,526 | 11/1972 | Sato et al. ......................... | 424/272 |

FOREIGN PATENTS OR APPLICATIONS

| | | | |
|---|---|---|---|
| 47-43809 | 6/1972 | Japan ................................ | 424/272 |

OTHER PUBLICATIONS

Chem. Abst. 58, 1463(d), Francais et al., "Plant Growth Stimulants."
Chem. Abst. 76 149465g, Fujinami et al. Antimicrobial Activity of–Compounds.
J.A.C.S. 81 6498–6504 (1959) Shapiro et al. "N–Substituted Oxazolidinediones."

*Primary Examiner*—Albert T. Meyers
*Assistant Examiner*—D. W. Robinson
*Attorney, Agent, or Firm*—Hammond & Littell

[57] ABSTRACT

Antiandrogenic compositions wherein the active principle is 3-(3',4'-dichlorophenyl)-5,5-dimethyl-oxazolidine-2,4-dione of the formula

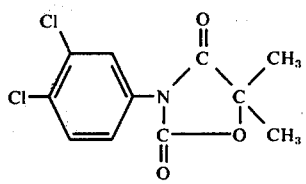

I are useful for inducing antiandrogenic activity in warm-blooded animals.

1 Claim, No Drawings

OXAZOLIDINE, 2-4 DIONES USEFUL AS ANTIANDROGENICS

STATE OF THE ART

Oxazolidines analogous to the compound of formula I have been described in JACS, Vol. 81 (1959), p. 6498–6504 as anticonvulsive agents. The product of formula I has also been described in the literature as a chemical compound having pesticidal properties such as fungicides and germicides. However, the pharmacological properties of the said product have not been known.

OBJECTS OF THE INVENTION

It is an object of the invention to provide novel antiandrogenic compositions.

It is another object of the invention to provide a novel method of inducing antiandrogenic activity in warm-blooded animals.

These and other objects and advantages of the invention will become obvious from the following detailed description.

THE INVENTION

The novel antiandrogenic compositions of the invention are comprised of an effective amount of 3-(3',4'-dichlorophenyl)-5,5 -dimethyl-oxazolidine-2,4-dione and a pharmaceutical carrier. The usual daily individual dose is 10 to 200 mg by oral route. The compositions may be in the form of injectable solutions or suspensions, tablets, coated tablets, capsules, syrups, suppositories, creams, pomades and lotions prepared in the usual manner.

The compositions inhibit the effects of androgens on peripheral receptors without causing harm to normal hypophysial functions. It may be used in the treatment in adolescents without fear of arresting their growth and in adults without having to fear certain effects of a chemical castration. The compositions may be used for the treatment of adenoma and neoplasia of the prostate, hirsutism, acne, seborrhea and hyperpilosity. The compositions are useful in human or animal medicine.

The active compound of formula I may be incorporated into the usual excipients such as aqueous or non-aqueous vehicles, talc, arabic gum, lactose, starch, magnesium stearate, cacao butter, fatty bodies of animal or vegetable origin, paraffinic derivatives, glycols, diverse wetting, emulsifying and dispersing agents or perservatives.

The novel method of the invention for inducing antiandrogenic activity in warm-blooded animals comprises administering to warm-blooded animals an antiandrogenically effective amount of 3-(3',4'-dichlorophenyl)-5,5-dimethyloxazolidine-2,4-dione. The said product may be administered orally, rectally, parenterally, perlingerally or topically. The usual useful daily dose is 0,2 to 4 mg/Kg by the oral route.

In the following examples there are described several preferred embodiments to illustrate the invention. However, it should be understood that the invention is not intended to be limited to the specific embodiments.

EXAMPLE 1

Tablets were prepared containing 20 mg of 3-(3',4'-dichlorophenyl)-5,5-dimethyl-oxazolidine-2,4-dione and sufficient excipient consisting of talc, lactose, starch and magnesium stearate to make a tablet weighing 100 mg.

EXAMPLE 2

The following tests were effected on castrated Sprague-Dawley rats by the scrotal route under ether anesthesia and the products were administered at a volume of 0.1 ml of a solution of sesame oil containing 5% benzyl alcohol.

A. Antiandrogenic Activity

Groups of 5 male castrated rats weighing 75 ± 5 g received daily for 7 days simultaneous subcutaneous administrations of 50 μg/rat/day of testosterone propionate and 1 mg per rat per day of the test product. The animals were killed 24 hours after the last administration and the prostate and the seminal vesicules were removed and fixed for 24 hours in an isotonic saline solution of 10% formol. The organs were then dissected and weighed. The inhibition of the weight increase of the genital organs induced by an androgen allowed the evaluation of the antiandrogenic activity of the test product.

The control groups did not receive any treatment while other groups received only testosterone propionate or the test product. The differences in weight of the prostate and the seminal vesicules were homogenized by logarithmitic transformation by the method of Bartlett (J. Roy. Stat. Soc., (1937) Supp. 4, p. 137) and the homogeneity was verified by the test of Bartlett [Biometrics, Vol. 3 (1947), p. 39] and the results were analyzed by factorial analysis and the results are reported in Table I.

TABLE I

| Products administered | Seminal Vesicules in mg | Ventral Prostate in mg |
|---|---|---|
| Controls | 8.12 ± 0.4 | 11.3 ± 0.6 |
| testosterone propionate | 88.2 ± 5.7 | 94.7 ± 4.6 |
| 3-(3',4'-dichlorophenyl)-5,5-dimethyl-oxazolidine-2,4-dione | 6.5 ± 0.4 | 8.9 ± 0.3 |
| testosterone propionate + 3-(3',4'-dichlorophenyl)-5,5-dimethyl-oxazolidine-2,4-dione | 13.7 ± 1.7* | 36.0 ± 2.5* |

*factorial analysis $p \leq 0.01$

The data of Table I shows that 3-(3',4'-dichlorophenyl)-5,5-dimethyl-oxazolidine-2,4-dione caused 93% inhibition of the weight increase in seminal vesicules and 70% in the prostate which means that the product shows a good anti-androgenic activity against testosterone propionate.

B. Inhibition of Prostatic incorporation of radioactivity after injection of a tracer dose of 3H-testosterone in rat:

Groups of 3 castrated male rats weight 70 ± 10 g received 24 hours after castration a subcutaneous injection of 5 mg of 3-(3',4'-dichlorophenyl)-5,5-dimethyl-oxazolidine-2,4-dione. 16 hours later, the animals received an intramuscular injection of 10 μCi/100 g of 1α³-H-testosterone (26 Ci/mmole) in an alcohol solution. The animals were killed 1 hour after the tritie hormone injection and the ventral prostate was removed, rinsed with an isotonic sodium chloride solution, weighed and solubilized by alkaline digestion. The radioactivity of samples was measured after addition of 15 ml of scintillating liquid and the results are expressed as percent of inhibition of incorporation of testosterone in Table II.

TABLE II

| Product | Incorporation d.p.m./mg* | Percentage d'inhibition |
|---|---|---|
| Controls | 151 ± 11 | — |
| 3-(3',4'-dichlorophenyl)-5,5-dimethyl-oxazolidine-2,4-dione | 55 ± 8 | 64% |

TABLE II-continued

| Product | Incorporation d.p.m./mg* | Percentage d'inhibition |
|---|---|---|

*d.p.m./mg = disintegration per minute per mg of fresh prostatic tissue.

Table II shows that the test product diminishes the incorporation of tritie hormone in the prostate.

Various modifications of the compositions and method of the invention may be made without departing from the spirit or scope thereof and it should be understood that the invention is intended to be limited only as defined in the appended claims.

We claim:

1. A method of inducing antiandrogenic activity in warm-blooded animals comprising administering to warm-blooded animals an antiandrogenically effective amount of 3-(3',4'-dichlorophenyl)-5,5-dimethyl-oxazolidine-2,4-dione.

* * * * *